United States Patent
Oester et al.

(10) Patent No.: US 8,623,786 B2
(45) Date of Patent: Jan. 7, 2014

(54) SULPHATES OF POLYHYDRIC ALCOHOLS, POLYOLS, SACCHARIDES AND POLYSACCHARIDES FOR AGRICULTURAL APPLICATIONS

(75) Inventors: Dean Oester, Cincinnati, OH (US);
Mike White, Cincinnati, OH (US);
Timothy Anderson, Hamilton, OH (US)

(73) Assignee: Cognis IP Management GmbH, Duesseldorf (DE)

( * ) Notice: Subject to any disclaimer, the term of this patent is extended or adjusted under 35 U.S.C. 154(b) by 164 days.

(21) Appl. No.: 13/054,991

(22) PCT Filed: Jul. 11, 2009

(86) PCT No.: PCT/EP2009/005049
§ 371 (c)(1),
(2), (4) Date: Jan. 20, 2011

(87) PCT Pub. No.: WO2010/009820
PCT Pub. Date: Jan. 28, 2010

(65) Prior Publication Data
US 2011/0124504 A1    May 26, 2011

Related U.S. Application Data

(60) Provisional application No. 61/082,277, filed on Jul. 21, 2008.

(51) Int. Cl.
*A01N 31/00* (2006.01)
*C07C 305/00* (2006.01)
*C07C 53/00* (2006.01)
*C08H 3/00* (2006.01)
*C11D 1/28* (2006.01)

(52) U.S. Cl.
USPC ............... 504/353; 554/90; 558/26; 558/31; 558/34

(58) Field of Classification Search
USPC .................. 504/353; 558/26, 31, 34
See application file for complete search history.

(56) References Cited

U.S. PATENT DOCUMENTS

| | | | | |
|---|---|---|---|---|
| 2,452,943 A * | 11/1948 | Malkemus et al. | ............. | 554/90 |
| 2,868,812 A | 1/1959 | Gray | | |
| 4,832,876 A * | 5/1989 | Ahmed | ............. | 554/90 |
| 5,117,032 A * | 5/1992 | Fabry et al. | ............. | 558/34 |
| 5,795,942 A | 8/1998 | Rhee et al. | | |
| 2008/0299222 A1* | 12/2008 | Crudden | ............. | 424/618 |

FOREIGN PATENT DOCUMENTS

| | | | |
|---|---|---|---|
| EP | 0532557 B2 | 3/1993 | |
| WO | WO2008/127661 A1 * | 10/2008 | ........ A01N 37/00 |

OTHER PUBLICATIONS

"1H- and 13C-NMR spectroscopy of synthetic monosulfated methyl α-D-mannopyranosides"; R. R. Contreras, et al.; Recueil des Travaux Chimiques des Pays-Bas, 110/3, Mar. 1991; pp. 85-88.

* cited by examiner

*Primary Examiner* — Jane C Oswecki
(74) *Attorney, Agent, or Firm* — Servilla Whitney LLC

(57) ABSTRACT

Disclosed is a process for preparing an adjuvant for agricultural applications, characterized in that a polyhydric alcohol, polyol, saccharide, or polysaccharide is reacted with a sulfonating agent, such as sulphamic acid.

20 Claims, 1 Drawing Sheet

Control of Velvet Leaf

Control of Velvet Leaf

SULPHATES OF POLYHYDRIC ALCOHOLS, POLYOLS, SACCHARIDES AND POLYSACCHARIDES FOR AGRICULTURAL APPLICATIONS

CROSS REFERENCE TO RELATED APPLICATIONS

This application is the National Phase entry of PCT Application No. PCT/EP2009/005049, filed Jul. 11, 2009, which claims priority to U.S. provisional Application No. 61/082,277, filed Jul. 21, 2008, both of which are incorporated herein by reference in their entireties.

FIELD OF THE INVENTION

The invention relates generally to adjuvants for agricultural sprays, and more particularly, to sulphated polyhydric alcohols, polyols, saccharides, and polysaccharides as adjuvants in agricultural spray applications. Agricultural spray applications include herbicides, insecticides, insect repellents, fungicides, and plant growth regulators.

BACKGROUND OF THE INVENTION

Agricultural spray applications have long included agents to amplify or accelerate the activity of the pesticidal active ingredient. These agents often include nitrogen based fertilizers such as UAN (Urea Ammonium Nitrate) or AMS (Ammonium Sulphate). Although the mechanism is debated the empirical evidence is strong that there is better uptake of selected active ingredients when nitrogen-based agents are incorporated. There are many different pesticide chemistries that include recommendations for addition of nitrogen-based adjuvants; however the greatest numbers of these are herbicides. Pesticides, which includes fungicides, herbicides, insecticides, algicides, moluscicides, miticides and rodenticides, are well known from the state of the art (here, The Pesticide Manual, $14^{th}$ edition, BCPC 2006, editor CDS Tomlin, is included as a reference, it provides information about the individual mode of actions of active ingredients).

Glyphosate (sodium 2-[(hydroxy-oxido-phosphoryl)methylamino]acetic acid or N(phosphonomethyl)glycine is a non-selective systemic herbicide. Glyphosate, one of the most widely used herbicides, is effective in killing a wide variety of plants, including grasses, broadleaf, and woody plants. Glyphosate is currently supplied in several formulations, including ammonium salt, isopropyl amine salt, potassium salt, and glyphosate acid. Glufosinate is another non-selective herbicide with a different mode of action than glyphosate because translocation only occurs within leaves. Commonly, it is available as ammonium salt.

Spray solutions comprising "hard water" and glyphosate have been demonstrated to have reduced control of unwanted vegetation. "Hard water" is water with high levels of calcium, magnesium, and/or sodium. Other cations may also contribute to hard water. It has been proposed that "hard water" in a spray tank reduces the effectiveness of glyphosate because the cations form a complex with the glyphosate molecule. Glyphosate acts as a chelator or a sequestering agent and forms complexes in the presence of calcium, iron, and magnesium ions. These complexes are incapable of penetrating the epidermal layers of plant leaves and thus reduce the effectiveness of glyphosate as a control agent in unwanted vegetation or weeds.

Adding agents such as ammonium sulphate, for example, to the spray tank, alleviates the problems associated with hard water, by sequestering the cations, and in turn "protecting" the herbicide to penetrate and translocate to the root system of the unwanted vegetation or weed. In addition to ammonium sulphate, phosphoric acid and citric acid are used to sequester, i.e., complex, hard water ions, including $Ca^{2+}$ and $Mg^{2+}$, by associating with the glyphosate molecule, thus preventing the $Ca^{2+}$ and $Mg^{2+}$ from doing so.

When ammonium (or other sequestering agent) is complexed with the glyphosate or glufosinate molecule, the molecule functions as intended. Large quantities of ammonium sulphate, i.e., 8.5 lbs to 17 lbs per 100 gallons of water (equivalent to 1 to 2 kg/100 l), are currently recommended to provide the desired effect. Ammonium sulphate is limited to water-based formulations. Adding ammonium sulphate may still be beneficial, even when the water is not hard. Some plants, for example, velvetleaf (*abutilon theophrastt*) contain high levels of calcium in intracellular spaces, and/or have natural defence mechanisms which may also reduce the effectiveness of glyphosate. The addition of ammonium sulphate in these situations also improves the effectiveness of glyphosate.

Many commercial crops have been genetically modified to tolerate glyphosate herbicide sprays, creating a global demand for glyphosate herbicide formulations. The commercial aqueous glyphosate formulation usually contains a surfactant, in addition to other additives, including humectants, anti-gelling agents and anti-freezing agents. The surfactant functions to increase surface wetting, and may also potentiate the active ingredient. Glycerol, a renewable resource, may be used as a humectant in such agricultural spray applications.

One negative effect of the presence of ammonium sulphate in a water spray solutions is its effect on the cloud point of surfactants due to increased electrolyte levels. This effect prevents the formation of stable liquid formulations of glyphosate with ammonium sulfate and a surfactant. Although ammonium sulphate is available in both dry and liquid (40%) forms, end users prefer liquid versions that offer some other functional additives. There are very few surfactants that can be blended with concentrated liquid ammonium sulphate and form single phase products, although alkyl polyglycoside may be added in amounts up to 20% with 40% ammonium sulphate.

What remains is a need for an effective replacement for ammonium sulphate and for suitable nitrogen based adjuvants in other agricultural applications, in particular to form a stable liquid formulation, preferentially containing glyphosate or glufosinate, optionally containing a surfactant to boost the respective biological efficacy, with a sequestering agent for cations, said sequestering agent enhancing the biological performance of active ingredients, too. It has been the object of the present invention to meet this desire of the market.

DETAILED DESCRIPTION OF THE INVENTION

Figure 1:
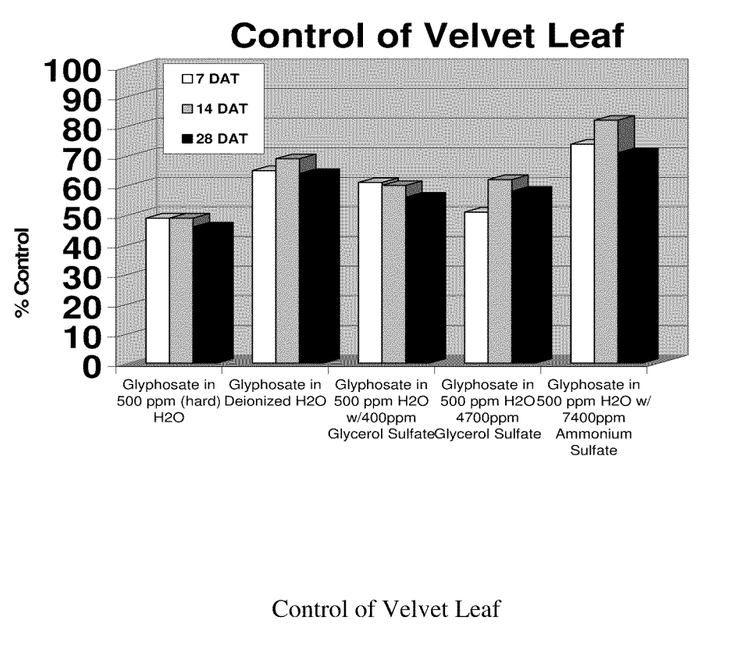
The FIGURE shows the control of the broadleaf weed velvetleaf with various glyphosate formulations.

In a first embodiment the present invention refers to a process for preparing an adjuvant for agricultural applications, characterized in that a polyhydric alcohol, polyol, saccharide, or polysaccharide is reacted with a sulphating agent, preferably with sulphamic acid.

Surprisingly applicants have observed that by reacting polyhydric alcohols, polyols, saccharides, or polysaccharides with an sulphation agent, preferably sulphamic acid, an improved sequestering potential is realized when the sulphated compounds are added to glyphosate, for example, as the multiple activity sites yield a more efficient sequesterant than ammonium sulphate. By sulphating molecules with one or more hydroxyl groups, one can obtain different degrees of sulphation being present in one product. In a preferred embodiment of the present invention, sulphated glycerol is used. Glycerol sulphate is known and described in U.S. Pat. No. 2,452,943, (Colgate) yet, it is restricted to its formation by using sulphamic acid with an amide as catalyst. EP 0532557 A1 (Henkel) teaches a process for making glycerol sulphate using gaseous sulphur trioxide. However, no reference to agricultural applications is made in these disclosures.

Sulphating Agents

Suitable sulphating agents encompass inter alia concentrated sulphuric acid, oleum, chlorosulphonic acid or $SO_3$ gas. Especially preferred is to use sulphamic acid, also known as amidosulphonic acid, amidosulphuric acid, aminosulphonic acid, and sulphamidic acid, is a weakly acidic, colourless, water-soluble compound according to the formula $H_3NSO_3$.

Surfactants

As set out above, the surfactants according to the present invention exhibit a significant adjuvant effect on biologically-active ingredients, such as for example herbicides, at in particular glyphosates (which also includes its salts, like for example sodium, potassium, lithium, ammonium, alkyl ammonium salt). The surfactants are obtained by reacting an alcoholic compound with sulfamic acid. Said alcoholic compound encompasses polyhydric alcohols, polyols, saccharides, polysaccharides and their mixtures. According to another aspect of the invention, the sulphates may be prepared by reacting polyhydric alcohols, polyols, saccharides, and to polysaccharides with concentrated sulphuric acid. In addition, the polyhydric alcohol, polyol, saccharide or polysaccharide starting material may be modified with agents (such as propylene oxide) to increase oil-solubility of the final sulphated product. In addition, the polyhydric alcohol, polyol, saccharide or polysaccharide starting material may be modified with agents (such as propylene oxide) to increase oil-solubility of the final sulphated product according to the standard procedures known from organic chemistry. To the extent solvents are present or even necessary, preferred examples comprise dialkyl amides, for example dimethyl amides of $C_{12}$-$C_{18}$ fatty acids, lactic acid or levulinic acid. It is understood that the scope of the present invention is not limited to monosulphates. Depending on the number of available hydroxyl group it also encompasses higher sulphates as for example disulphates, trisulphates and the like and their mixtures.

Polyhydric Alcohols

Suitable polyhydric alcohols include but are not limited to diols, for example, propylene glycol, and ethylene glycol. Other suitable polyhydric alcohols may include longer carbon chains such as diethylene glycol, hexylene glycol and decalene glycol, glycerol, polyglycerol and their mixtures. The carbon chain length of the polyhydric alcohol will generally not exceed about 14 carbon atoms, and preferably contains 2 to 10, more preferably 3 to 6 carbon atoms, as viscosity may become prohibitively high, and water-solubility too low for miscibility in the spray solution.

Polyols and Saccharides

Suitable polyols include, but are not limited to, for example, polypropylene glycol, polyethylene glycol, and their mixtures. The polyol typically contain 2 to 30 and preferably 3 to 10 carbon atoms. Suitable saccharides include, but are not limited to, for example, monosaccharides disaccharides, polysaccharides and their mixtures.

The surfactant component may also be a mixture of mono-, di-, and tri-sulphated polyhydric alcohols or polyols, and may also be a mixture of predominantly mono- and di-sulphates. Thoughtful selection of the starting backbone will lead to oil- or water-miscible molecules which as ammonium salts of sulphates will still function as sequestering agents. Addition of propylene oxide, ethylene oxide, polypropylene glycol or polyethylene glycol to one of the free hydroxyl groups counteracts the hydrophilicity of the sulphate created by reaction with sulphamic acid to allow a range of water/oil solubility of the final product. This allows the formulator of hydrolytically unstable pesticides (such as sulphonyl-urea herbicides) to create oil-continuous formulations which include the desired adjuvant. The oil-continuous sulphates become biologically/chemically active adjuvants when diluted into the water rich spray solution at the time of final application. Applicants have advantageously found that oleo-sulphates, based on glycerol, are miscible with all surfactants. When glycerol is selected for use according to an aspect of the invention, the glycerol may be crude or U.S.P. grade, with up to three sulphate groups on the glycerol molecule. Applicants have also advantageously found that glycerol sulphate has blended with every surfactant tested. Surfactants successfully blended include: alkylphenol ethoxylates, alkyl polyglycosides, tallow amine ethoxylates, sorbitan esters, fatty acid esters of glycerol, PEG esters of fatty acids, phosphate esters of alcohols and ethoxylates thereof), amine oxides, alkyl ether sulphates and alcohol ethoxylates. It may also be blended into potassium and isopropylamine salts of glyphosate without any separation. As with ammonium sulphate, the biological effect provided by the invention and compositions including the claimed molecules is more than sequestering of "hard water" cations. The nitrogen effect stimulates the plant and enhances uptake, translocation and deployment of many pesticidal active ingredients that have no chelating potential. A suitable ratio of about 0.9 moles to 4.0 moles of sulphamic acid to 1 mole of glycerol may be used according to an aspect of the invention. Analysis by Carbon-13 and Attached Proton NMR revealed that the increasing molar ratios of sulphamic acid synthesized amounts of mono-, di- and tri-substituted glycerol with ranges as follows. The invention includes compositions of free glycerol between 3% and 20%, glycerol monosulphate between 12% and 60%, glycerol disulphate between 8% and 20%, and glycerol trisulphate is nil to 20%. Inclusion of a catalyst (acetamide or urea) yielded product that comprised free glycerol between 1% and 15%, glycerol monosulphate between 1% and 35%, glycerol disulphate between 1% and 35%, and glycerol trisulphate is 24%-97%. Both were tested for efficacy with glyphosate in 500 ppm water (250 ppm Ca, 250 ppm Mg). Both improved the control of weeds over 500 ppm water with no additive, as illustrated in the FIGURE.

Advantageously, the order of addition has no effect on the efficacy of the adjuvant. There was also no observed difference between glyphosate treatments made whether the invention was formulated into the glyphosate concentrate or added to existing commercial products at the point of application, commonly referred to as tank mix. Products of the present invention can be combined with other surfactants in pesticide formulation, in particular, glufosinate and glyphosate. For the latter non-selective herbicide, alkyl polyglucosides, amine ethoxylates based on coco or tallow or a phosphorylated derivative, betaines such as trialkyl or cocoamidopropyl betaines, or an amine oxide can be used.

Biologically Active Compositions

Another object of the present invention refers to biologically-active compositions, comprising:
(a) surfactants obtained by reacting alcoholic compounds as set out above with sulfamic acid,
(b) biologically-active ingredients, and optionally
(c) auxiliary agents, like for example co-surfactants, emulsifiers or oil components.

The compositions may include components (a) and (b) in ratios by weight of about 10:90 to about 90:10, preferably about 25:75 to 75:25 and more preferably about 40:60 to 60:40. The compositions may be non-aqueous or contain water or polyols, such as for example glycerol or lower glycols. In amounts up to 50% b.w. The preferred surfactants (component a) are selected from the group consisting of sulphated polyhydric alcohols, sulphated polyols, sulphated saccharides, sulphated polysaccharides and their mixtures. Most preferred is glycerol sulphate.

Biologically-Active Ingredients

A biologically-active ingredient or—as a synonym—a biocide in the context of the present invention is a plant protection agent, more particular a chemical substance capable of killing different forms of living organisms used in fields such as medicine, agriculture, forestry, and mosquito control. Also counted under the group of biocides are so-called plant growth regulators. Usually, biocides are divided into two sub-groups:

pesticides, which includes fungicides, herbicides, insecticides, algicides, moluscicides, miticides and rodenticides, (here, The Pesticide Handbook, 14th edition, BCPC 2006 is included as a reference) and antimicrobials, which includes germicides, antibiotics, antibacterials, antivirals, antifungals, antiprotozoals and antiparasites.

Biocides can also be added to other materials (typically liquids) to protect the material from biological infestation and growth. For example, certain types of quaternary ammonium compounds (quats) can be added to pool water or industrial water systems to act as an algicide, protecting the water from infestation and growth of algae.

Pesticides

The U.S Environmental Protection Agency (EPA) defines a pesticide as "any substance or mixture of substances intended for preventing, destroying, repelling, or mitigating any pest". A pesticide may be a chemical substance or biological agent (such as a virus or bacteria) used against pests including insects, plant pathogens, weeds, mollusks, birds, mammals, fish, nematodes (roundworms) and microbes that compete with humans for food, destroy property, spread disease or are a nuisance. In the following examples, pesticides suitable for the agrochemical compositions according to the present invention are given:

Fungicides.

A fungicide is one of three main methods of pest control—the chemical control of fungi in this case. Fungicides are chemical compounds used to prevent the spread of fungi in gardens and crops. Fungicides are also used to fight fungal infections. Fungicides can either be contact or systemic. A contact fungicide kills fungi when sprayed on its surface. A systemic fungicide has to be absorbed by the fungus before the fungus dies. Examples for suitable fungicides, according to the present invention, encompass the following chemical classes and corresponding examples:

Aminopyrimidines such as bupirimate,
Anilinopyrimidines such as cyprodinil, mepanipyrim, pyrimethanil,
Heteroaromatics such as hymexazol,
Heteroaromatic hydrocarbons such as etridiazole,
Chlorophenyls/Nitroanilines such as chloroneb, dicloran, quintozene, tecnazene, tolclofos-methyl,
Benzamide fungicides such as zoxamide,
Benzenesulfonamides such as flusulfamide,
Benzimidazoles such as acibenzolar, benomyl, benzothiazole, carbendazim, fuberidazole, metrafenone, probenazole, thiabendazole, triazoxide, and benzimidazole precursor fungicides,
Carbamates such as propamocarb, diethofencarb,
Carboxamides such as boscalid, diclocymet, ethaboxam, flutolanil, penthiopyrad, thifluzamide
Chloronitriles such chlorothalonil,
Cinnamic acid amides such as dimethomorph, flumorph,
Cyanoacetamide oximes such as cymoxanil,
Cyclopropancarboxamides such as carpropamid,
Dicarboximides such as iprodione, octhilinone, procymidone, vinclozolin
Dimethyldithiocarbamates such ferbam, metam, thiram, ziram,
Dinitroanilines such as fluazinam,
Dithiocarbamates such as mancopper, mancozeb, maneb, metiram, nabam, propineb, zineb,
Dithiolanes such as isoprothiolane,
Glucopyranosyl antibiotics such as streptomycin, validamycin,
Guanidines such as dodine, guazatine, iminoctadine,
Hexopyranosyl antibiotics such as kasugamycin,
Hydroxyanilides such as fenhexamid,
Imidazoles such as imazalil, oxpoconazole, pefurazoate, prochloraz, triflumizole,
Imidazolinones such as fenamidone,
Inorganics such as Bordeaux mixture, copper hydroxide, copper naphthenate, copper oleate, copper oxychloride, copper(II) sulfate, copper sulfate, copper(II) acetate, copper(II) carbonate, cuprous oxide, sulfur,
Isobenzofuranones such as phthalide,
Mandelamides such as mandipropamide,
Morpholines such as dodemorph, fenpropimorph, tridemorph, fenpropidin, piperalin, spiroxamine, aldimorph
Organotins such as fentin,
Oxazolidinones such as oxadixyl,
Phenylamides such as benalaxyl, benalaxyl-M, furalaxyl, metalaxyl, metalaxyl-M, ofurace,
Phenylpyrazoles such as fipronil,
Phenylpyrroles such as fludioxonil,
Phenylureas such as pencycuron,
Phosphonates such fosetyl,
Phthalamic acids such as tecloftalam,
Phthalimides such as captafol, captan, folpet,
piperazines such as triforine,
Propionamides such as fenoxanil,
Pyridines such as pyrifenox,
Pyrimidines such as fenarimol, nuarimol,
Pyrroloquinolinones such as pyroquilon,
Qils such as cyazofamid,
Quinazolinones such as proquinazid,
Quinolines such as quinoxyfen,
Quinones such as dithianon,
Sulfamides such as tolylfluanid, dichlofluanid,
Strobilurines such as azoxystrobin, dimoxystrobin, famoxadone, fluoxastrobin, kresoxim-methyl, metominostrobin, picoxystrobin, pyraclostrobin, trifloxystrobin, orysastrobin,
Thiocarbamates such as methasulfocarb,
Thiophanates such as thiophanate-methyl,
Thiophencarboxamides such silthiofam, Triazole fungicides such as azaconazole, bitertanol, bromuconazole, cyproconazole, difenoconazole, diniconazole, epoxiconazole, fenbuconazole, fluquinconazole, flusilazole, flutriafol, fluotrimazole, hexaconazole, imibenconazole, ipconazole, metconazole, myclobutanil, penconazole, propiconazole, prothioconazole, simeconazole, tebuconazole, tetraconazole, triadimefon, triadimenol, triticonazole, quinconazole Triazolobenzothidazoles such as tricyclazole, Valinamide carbamates such as iprovalicarb, benthiavalicarb Fluopicolide Pentachlorophenol and their mixtures.

Herbicides.

An herbicide is a pesticide used to kill unwanted plants. Selective herbicides kill specific targets while leaving the desired crop relatively unharmed. Some of these act by interfering with the growth of the weed and are often based on plant hormones. Herbicides used to clear waste ground are nonselective and kill all plant material with which they come into contact. Herbicides are widely used in agriculture and in landscape turf management. They are applied in total vegetation control (TVC) programs for maintenance of highways and railroads. Smaller quantities are used in forestry, pasture systems, and management of areas set aside as wildlife habitat. In general, active ingredients representing including various chemical classes and corresponding examples can be used Anilides such as propanil Aryloxycarboxylic acids e.g. MCPA-thioethyl Aryloxyphenoxypropionates e.g. clodinafop-propargyl, cyhalofop-butyl, diclofops, fluazifops, haloxyfops, quizalofops, Chloroacetamides e.g. acetolochlor, alachlor, butachlor, dimethenamid, metolachlor, propachlor Cyclohexanedione oximes e.g. clethodim, sethoxydim, tralkoxydim, Benzamides such as isoxaben Benzimidazoles such as dicamba, ethofumesate Dinitroanilines e.g. trifluralin, pendimethalin, Diphenyl ethers e.g. aclonifen, oxyfluorfen, The glycine derivative glyphosate, a systemic nonselective (it kills any type of plant) herbicide used in no-till burndown and for weed control in crops that are genetically modified to resist its effects, Hydroxybenzonitriles e.g. bromoxynil, Imidazolinones e.g. fenamidone, imazapic, imazamox, imazapic, imazapyr, imazaquin, Isoxazolidinones e.g. clomazone Paraquat as bypyridylium, Phenyl carbamates e.g. desmedipham, phenmedipham, Phenylpyrazoles e.g. pyraflufen-ethyl Phenylpyrazolines e.g. pinoxaden, Pyridinecarboxylic acids or synthetic auxins e.g. picloram, clopyralid, and triclopyr, Pyrimidinyloxybenzoics e.g. bispyrtbac-sodium Sulfonyureas e.g. amidosulfuron, azimsulfuron, bensulfuron-methyl, chlorsulfuron, flazasulfuron, foramsulfuron, flupyrsulfuron-methyl-sodium, nicosulfuron, rimsulfuron, sulfosulfuron, tribenuron-methyl, trifloxysurlfuron-sodium, triflusulfuron, tritosulfuron, Triazolopyrimidines e.g. penoxsulam, metosulam, florasulam, Triketones e.g. mesotriones, sulcotrione, Ureas e.g. diuron, linuron, Phenoxycarboxylic acids such as 2,4-D, MCPA, MCPB, mecoprops, Triazines such as atrazine, simazine, terbuthylazine, and their mixtures.

Insecticides.

An insecticide is a pesticide used against insects in all developmental forms. They include ovicides and larvicides used against the eggs and larvae of insects. Insecticides are used in agriculture, medicine, industry and the household. In the following, suitable chemical classes and examples of insecticides are mentioned:

Abamectin, emamectin,

Anthranilic diamides such as rynaxypyr

Synthetic auxins Duch as avermectin,

Amidines such as amitraz,

Anthranilic diamide Duch as rynaxypyr,

Carbamates such as aldicarb, carbofuran, carbaryl, methomyl, 2-(1-methylpropyl)phenyl methylcarbamate, Chlorinated insecticides such as, for example, Camphechlor, DDT, Hexachlorocyclohexane, gamma-Hexachlorocyclohexane, Methoxychlor, Pentachlorophenol, TDE, Aldrin, Chlordane, Chlordecone, Dieldrin, Endosulfan, Endrin, Heptachlor, Mirex, Juvenile hormone mimics such as pyriproxyfen, Neonicotinoids such as imidacloprid, clothianidin, thiacloprid, thiamethoxam, Organophosphorus compounds such as acephate, azinphos-methyl, bensulide, chlorethoxyfos, chlorpyrifos, chlorpyriphos-methyl, diazinon, dichlorvos (DDVP), dicrotophos, dimethoate, disulfoton, dthoprop, fenamiphos, fenitrothion, fenthion, fosthiazate, malathion, methamidophos, methidathion, methyl-parathion, mevinphos, naled, omethoate, oxydemeton-methyl, parathion, phorate, phosalone, phosmet, phostebupirim, pirimiphos-methyl, profenofos, terbufos, tetrachlorvinphos, tribufos, trichlorfon, Oxadiazines such as indoxacarb, Plant toxin derived compounds such as derris (rotenone), pyrethrum, neem (azadirachtin), nicotine, caffeine, Pheromones such cuellure, methyl eugenol, Pyrethroids such as, for example, allethrin, bifenthrin, deltamethrin, permethrin, resmethrin, sumithrin, tetramethrin, tralomethrin, transfluthrin, Selective feeding blockers such as flonicamid, pymetrozine, Spinosyns e.g. spinosad and their mixtures.

Plant Growth Regulators.

Plant hormones (also known as phytohormones) are chemicals that regulate plant growth. Plant hormones are signal molecules produced within the plant, and occur in extremely low concentrations. Hormones regulate cellular processes in targeted cells locally and when moved to other locations, in other locations of the plant. Plants, unlike animals, lack glands that produce and secrete hormones. Plant hormones shape the plant, affecting seed growth, time of flowering, the sex of flowers, senescence of leaves and fruits. They affect which tissues grow upward and which grow downward, leaf formation and stem growth, fruit development and ripening, plant longevity and even plant death. Hormones are vital to plant growth and lacking them, plants would be mostly a mass of undifferentiated cells. In the following, suitable plant growth regulators are mentioned:

Aviglycine,

Cyanamide,

Gibberellins such gibberellic acid,

Quaternary ammoniums such as chlormequat chloride, mepiquat chloride,

Ethylene generators such ethephone,

Rodenticides.

Rodenticides are a category of pest control chemicals intended to kill rodents. Rodents are difficult to kill with poisons because their feeding habits reflect their place as scavengers. They would eat a small bit of something and wait, and if they do not get sick, they would continue eating. An effective rodenticide must be tasteless and odorless in lethal concentrations, and have a delayed effect. In the following, examples for suitable rodenticides are given:

Anticoagulants are defined as chronic (death occurs after 1-2 weeks post ingestion of the lethal dose, rarely sooner), single-dose (second generation) or multiple dose (first generation) cumulative rodenticides. Fatal internal bleeding is caused by lethal dose of anticoagulants such as brodifacoum, coumatetralyl or warfarin. These substances in effective doses are antivitamins K, blocking the enzymes $K_1$-2,3-epoxide-reductase (this enzyme is preferentially blocked by 4-hydroxycoumarin/4-hydroxythiacoumarin derivatives) and $K_1$-quinone-reductase (this enzyme is preferentially blocked by indandione derivatives), depriving the organism of its source of active vitamin $K_1$. This leads to a disruption of the vitamin K cycle, resulting in an inability of production of essential blood-clotting factors (mainly coagulation factors II (prothrombin), VII (proconvertin), IX (Christmas factor) and X (Stuart factor)). In addition to this specific metabolic disruption, toxic doses of 4-hydroxycoumarin/4-hydroxythiacoumarin and indandione anticoagulants are causing damage to tiny blood vessels (capillaries), increasing their permeability, causing diffuse internal bleedings (haemorrhagias). These effects are gradual; they develop in the course of days and are not accompanied by any nociceptive perceptions, such as pain or agony. In the final phase of intoxication the exhausted rodent collapses in hypovolemic circulatory shock or severe anemia and dies calmly. Rodenticidal anticoagulants are either first generation agents (4-hydroxycoumarin type: warfarin, coumatetralyl; indandione type: pindone, diphacinone, chlorophacinone), generally requiring higher concentrations (usually between 0.005 and 0.1%), consecutive intake over days in order to accumulate the lethal dose, poor active or inactive after single feeding and less toxic than second generation agents, which are derivatives of 4-hydroxycoumarin (difenacoum, brodifacoum, bromadiolone and flocoumafen) or 4-hydroxy-1-benzothiin-2-one (4-hydroxy-1-thiacoumarin, sometimes incorrectlly referred to as 4-hydroxy-1-thiocoumarin, for reason see heterocyclic compounds), namely difethialone. Second generation agents are far more toxic than first generation agents, they are generally applied in lower concentrations in baits (usually in the order of 0.001-0.005%), and are lethal after single ingestion of bait and are effective also against strains of rodents that have become resistant against first generation anticoagulants; thus the second generation anticoagulants are sometimes referred to as "superwarfarins". Sometimes, anticoagulant rodenticides are potentiated by an antibiotic, most commonly by sulfaquinoxaline. The aim of this association (e.g. warfarin 0.05%+sulfaquinoxaline 0.02%, or difenacoum 0.005%+sulfaquinoxaline 0.02% etc.) is that the antibiotic/bacteriostatic agent suppresses intestinal/gut symbiotic microflora that represents a source of vitamin K. Thus the symbiotic bacteria are killed or their metabolism is impaired and the production of yltamin K by them is dim inuted, an effect which logically contributes to the action of anticoagulants. Antibiotic agents other than sulfaquinoxaline may be used, for example co-trimoxazole, tetracycline, neomycin or metronidazole. A further synergism used in rodenticidal baits is that of an association of an anticoagulant with a compound with vitamin D-activity, i.e. cholecalciferol or ergocalciferol (see below). A typical formula used is, e.g., warfarin 0.025-0.05%+cholecalciferol 0.01%. In some countries there are even fixed three-component rodenticides, i.e. anticoagulant+antibiotic+vitamin D, e.g. difenacoum 0.005%+sulfaquinoxaline 0.02%+cholecalciferol 0.01%. Associations of a second-generation anticoagulant with an antibiotic and/or vitamin D are considered to be effective even against the most resistant strains of rodents, though some second generation anticoagulants (namely brodifacoum and difethialone), in bait concentrations of 0.0025-0.005% are so toxic that no known resistant strain of rodents exists and even rodents resistant against any other derivatives are reliably exterminated by application of these most toxic anticoagulants.

Vitamin $K_1$ has been suggested and successfully used as an antidote for pets or humans, which/who were either accidentally or intentionally (poison assaults on pets, suicidal attempts) exposed to anticoagulant poisons. In addition, since some of these poisons act by inhibiting liver functions and in progressed stages of poisoning, several blood-clotting factors as well as the whole volume of circulating blood lacks, a blood transfusion (optionally with the clotting factors present) can save a person's life who inadvertently takes them, which is an advantage over some older poisons.

Metal phosphides have been used as a means of killing rodents and are considered single-dose fast acting rodenticides (death occurs commonly within 1-3 days after single bait ingestion). A bait consisting of food and a phosphide (usually zinc phosphide) is left where the rodents can eat it. The acid in the digestive system of the rodent reacts with the phosphide to generate the toxic phosphine gas. This method of vermin control has possible use in places where rodents are resistant to some of the anticoagulants, particularly for control of house and field mice; zinc phosphide baits are also cheaper than most second-generation anticoagulants, so that sometimes, in cases of large infestation by rodents, their population is initially reduced by copious amounts of zinc phosphide bait applied, and the rest of the population that survived the initial fastacting poison is then eradicated by prolonged feeding on anticoagulant bait. Inversely, the individual rodents that survived anticoagulant bait poisoning (rest population) can be eradicated by pre-baiting them with nontoxic bait for a week or two (this is important to overcome bait shyness, and to get rodents used to feeding in specific areas by offering specific food, especially when eradicating rats) and subsequently applying poisoned bait of the same sort as used for pre-baiting until all consumption of the bait ceases (usually within 2-4 days). These methods of alternating rodenticides with different modes of action provides a factual or an almost 100% eradication of the rodent population in the area if the acceptance/palatability of bait is good (i.e., rodents readily feed on it).

Phosphides are rather fast acting rat poisons, resulting in that the rats are dying usually in open areas instead of the affected buildings. Typical examples are aluminum phosphide (fumigant only), calcium phosphide (fumigant only), magnesium phosphide (fumigant only) and zinc phosphide (in baits). Zinc phosphide is typically added to rodent baits in amounts of around 0.75-2%. The baits have a strong, pungent garlic-like odor characteristic for phosphine liberated by hydrolysis. The odor attracts (or, at least, does not repulse) rodents, but has a repulsive effect on other mammals; birds, however (notably wild turkeys), are not sensitive to the smell and feed on the bait thus becoming collateral damage.

Hypercalcemia. Calciferols (vitamins D), cholecalciferol (vitamin $D_3$) and ergocalciferol (vitamin $D_2$) are used as rodenticides, which are toxic to rodents for the same reason that they are beneficial to mammals: they are affecting calcium and phosphate homeostasis in the body. Vitamins D are essential in minute quantities (few Ws per kilogram body weight daily, which is only a fraction of a milligram), and like most fat soluble vitamins they are toxic in larger doses as they readily result in the so-called hypervitaminosis, which is, simply said, poisoning by the vitamin. If the poisoning is severe enough (that is, if the dose of the toxicant is high enough), it eventually leads to death. In rodents consuming the rodenticidal bait it causes hypercalcemia by raising the calcium level, mainly by increasing calcium absorption from food, mobilising bone-matrix-fixed calcium into ionised form (mainly monohydrogencarbonate calcium cation, partially bound to plasma proteins, $[CaHCO_3]^+$), which circulates dissolved in the blood plasma, and after ingestion of a lethal dose the free calcium levels are raised sufficiently so that blood vessels, kidneys, the stomach wall and lungs are mineralised/calcificated (formation of calcificates, crystals of calcium salts/complexes in the tissues thus damaging them), leading further to heart problems (myocard is sensitive to variations of free calcium levels that are affecting both myocardial contractibility and excitation propagation between atrias and ventriculas) and bleeding (due to capillary damage) and possibly kidney failure. It is considered to be single-dose, or cumulative (depending on concentration used; the common 0.075% bait concentration is lethal to most rodents after a single intake of larger portions of the bait), sub-chronic (death occurring usually within days to one week after ingestion of the bait). Applied concentrations are 0.075% cholecalciferol and 0.1% ergocalciferol when used alone. There is an important feature of calciferols toxicology which is that they are synergistic with anticoagulant toxicants. This means that mixtures of anticoagulants and calciferols in the same bait are more toxic than the sum of toxicities of the anticoagulant and the calciferol in the bait so that a massive hypercalcemic effect can be achieved by a substantially lower calciferol content in the bait and vice-versa. More pronounced anticoagulant/hemorrhagic effects are observed if calciferol is present. This synergism is mostly used in baits low in calciferol because effective concentrations of calciferols are more expensive than effective concentrations of most anticoagulants. The historically very first application of a calciferol in rodenticidal bait was, in fact, the Sorex product Sorexa® D (with a different formula than today's Sorexa® D) back in the early 1970's, containing warfarin 0.025%+ergocalciferol 0.1%. Today, Sorexa® CD contains a 0.0025% difenacoum+0.075% cholecalciferol combination. Numerous other brand products containing either calciferols 0.075-0.1% (e.g. Quintox®, containing 0.075% cholecalciferol) alone, or a combination of calciferol 0.01-0.075% with an anticoagulant are marketed.

Miticides, Moluscicides and Nematicides.

Miticides are pesticides that kill mites. Antibiotic miticides, carbamate miticides, formamidine miticides, mite growth regulators, organochlorine, permethrin and organophosphate miticides all belong to this category. Molluscicides are pesticides used to control mollusks, such as moths, slugs and snails. These substances include metaldehyde, methiocarb and aluminium sulfate. A nematicide is a type of chemical pesticide used to kill parasitic nematodes (a phylum of worm). A nematicide is obtained from a neem tree's seed cake; which is the residue of neem seeds after oil extraction. The neem tree is known by several names in the world but was first cultivated in India since ancient times.

Antimicrobials

In the following examples, antimicrobials suitable for agrochemical compositions according to the present invention are given. Bactericidal disinfectants mostly used are those applying active chlorine (i.e., hypochlorites, chloramines, dichloroisocyanurate and trichloroisocyanurate, wet chlorine, chlorine dioxide, etc.), active oxygen (peroxides such as peracetic acid, potassium persulfate, sodium perborate, sodium percarbonate and urea perhydrate), iodine (iodpovidone (povidone-iodine, Betadine), Lugol's solution, iodine tincture, iodinated nonionic surfactants), concentrated alcohols (mainly ethanol, 1-propanol, called also n-propanol and 2-propanol, called isopropanol and mixtures thereof; further, 2-phenoxyethanol and 1- and 2-phenoxypropanols are used), phenolic substances (such as phenol (also called "carbolic acid"), cresols (called "Lysole" in combination with liquid potassium soaps), halogenated (chlorinated, brominated) phenols, such as hexachlorophene, triclosan, trichlorophenol, tribromophenol, pentachlorophenol, Dibromol and salts thereof), cationic surfactants such as some quaternary ammonium cations (such as benzalkonium chloride, cetyl trimethylammonium bromide or chloride, didecyldimethylammonium chloride, cetylpyridinium chloride, benzethonium chloride) and others, non-quarternary compounds such as chlorhexidine, glucoprotamine, octenidine dihydrochloride, etc.), strong oxidizers such as ozone and permanganate solutions;

heavy metals and their salts such as colloidal silver, silver nitrate, mercury chloride, phenylmercury salts, copper sulfate, copper oxide-chloride etc. Heavy metals and their salts are the most toxic and environmentally hazardous bactericides and, therefore, their use is strongly suppressed or forbidden; further, also properly concentrated strong acids (phosphoric, nitric, sulfuric, amidosulfuric, toluenesulfonic acids) and alcalis (sodium, potassium, calcium hydroxides) between pH <1 or >13, particularly below elevated temperatures (above 60° C.) kill bacteria.

As antiseptics (i.e., germicide agents that can be used on human or animal body, skin, mucoses, wounds and the like), few of the above mentioned disinfectants can be used under proper conditions (mainly concentration, pH, temperature and toxicity toward man/animal). Among them, important are Some properly diluted chlorine preparations (e.g. Daquin's solution, 0.5% sodium or potassium hypochlorite solution, pH-adjusted to pH 7-8, or 0.5-1% solution of sodium benzenesulfochloramide (chloramine B)), some iodine preparations such as iodopovidone in various galenics (ointments, solutions, wound plasters), in the past also Lugol's solution, peroxides as urea perhydrate solutions and pH-buffered 0.1-0.25% peracetic acid solutions, alcohols with or without antiseptic additives, used mainly for skin antisepsis, weak organic acids such as sorbic acid, benzoic acid, lactic acid and salicylic acid some phenolic compounds such as hexachlorophene, triclosan and Dibromol, and cation-active compounds such as 0.05-0.5% benzalkonium, 0.5-4% chlorhexidine, 0.1-2% octenidine solutions.

Bactericidal antibiotics kill bacteria; bacteriostatic antibiotics only slow down their growth or reproduction. Penicillin is a bactericide, as are cephalosporins. Aminoglycosidic antibiotics can act in both a bactericidic manner (by disrupting cell wall precursor leading to lysis) or bacteriostatic manner (by connecting to 30s ribosomal subunit and reducing translation fidelity leading to inaccurate protein synthesis). Other bactericidal antibiotics according to the present invention include the fluoroquinolones, nitrofurans, vancomycin, monobactams, co-trimoxazole, and metronidazole Preferred actives are those with systemic or partially systemic mode of action such as for example azoxystrobin.

The preferred biologically active ingredients (=biocides), however, are selected from the group consisting of insecticides, herbicides, fungicides and plant growth promoters. In particular preferred compositions comprise glyphosate acid or glufosinate and its derivatives, especially its salt derivatives.

Co-Surfactants and Emulsifiers

In a number of cases it is advantageous to add co-surfactants or emulsifiers (optional component c2) to the biocide compositions in order to support the stability of the products. A first preferred group of emulsifiers encompasses non-ionic surfactants such as, for example:

products of the addition of 2 to 30 mol ethylene oxide and/or 0 to 5 mol propylene oxide onto linear $C_{8-22}$ fatty alcohols, onto $C_{12-22}$ fatty acids and onto alkyl phenols containing 8 to 15 carbon atoms in the alkyl group;

$C_{12/18}$ fatty acid monoesters and diesters of addition products of 1 to 30 mol ethylene oxide onto glycerol;

glycerol mono- and diesters and sorbitan mono- and diesters of saturated and unsaturated fatty acids containing 6 to 22 carbon atoms and ethylene oxide addition products thereof;

addition products of 15 to 60 mol ethylene oxide onto castor oil and/or hydrogenated castor oil;

polyol esters and, in particular, polyglycerol esters such as, for example, polyglycerol polyricinoleate, polyglycerol poly-12-hydroxystearate or polyglycerol dimerate isostearate. Mixtures of compounds from several of these classes are also suitable;

addition products of 2 to 15 mol ethylene oxide onto castor oil and/or hydrogenated castor oil;

partial esters based on linear, branched, unsaturated or saturated $C_{6/22}$ fatty acids, ricinoleic acid and 12-hydroxystearic acid and glycerol, polyglycerol, pentaerythritol, dipentaerythritol, sugar alcohols (for example sorbitol), alkyl glucosides (for example methyl glucoside, butyl glucoside, lauryl glucoside) and polyglucosides (for example cellulose);

alkoxylatation products of saccharose esters mono-, di and trialkyl phosphates and mono-, di- and/or tri-PEG-alkyl phosphates and salts thereof;

wool wax alcohols;

polysiloxane/polyalkyl polyether copolymers and corresponding derivatives;

mixed esters of pentaerythritol, fatty acids, citric acid and fatty alcohol and/or mixed esters of $C_{6-22}$ fatty acids, methyl glucose and polyols, preferably glycerol or polyglycerol, polyalkylene glycols and glycerol carbonate.

The addition products of ethylene oxide and/or propylene oxide onto fatty alcohols, fatty acids, alkylphenols, glycerol mono- and diesters and sorbitan mono- and diesters of fatty acids or onto castor oil are known commercially available products. They are homologue mixtures of which the average degree of alkoxylation corresponds to the ratio between the quantities of ethylene oxide and/or propylene oxide and substrate with which the addition reaction is carried out. $C_{12/18}$ fatty acid monoesters and diesters of addition products of ethylene oxide onto glycerol are known as lipid layer enhancers for cosmetic formulations. The preferred emulsifiers are described in more detail as follows:

Partial Glycerides

Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride and technical mixtures thereof which may still contain small quantities of triglyceride from the production process. Addition products of 1 to 30, and preferably 5 to 10, mol ethylene oxide onto the partial glycerides mentioned are also suitable.

Sorbitan Esters

Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. Addition products of 1 to 30, and preferably 5 to 10, mol ethylene oxide onto the sorbitan esters mentioned are also suitable.

Polyglycerol Esters

Typical examples of suitable polyglycerol esters are Polyglyceryl-2 Dipolyhydroxystearate (Dehymuls® PGPH), Polyglycerin-3-Diisostearate (Lameform® TGI), Polyglyceryl-4 Isostearate (Isolan® GI 34), Polyglyceryl-3 Oleate, Diisostearoyl Polyglyceryl-3 Diisostearate (Isolan® PDI), Polyglyceryl-3 Methylglucose Distearate (Tego Care® 450), Polyglyceryl-3 Beeswax (Cera Bellina®), Polyglyceryl-4 Caprate (Polyglycerol Caprate T2010/90), Polyglyceryl-3 Cetyl Ether (Chimexane® NL), Polyglyceryl-3 Distearate (Cremophor® GS 32) and Polyglyceryl Polyricinoleate (Admul® WOL 1403), Polyglyceryl Dimerate Isostearate and mixtures thereof. Examples of other suitable polyesters are the mono-, di- and triesters of trimethylol propane or pentaerythritol with lauric acid, cocofatty acid, tallow fatty acid, palmitic acid, stearic acid, oleic acid, behenic acid and the like, optionally reacted with 1 to 30 mol ethylene oxide.

Alk(en)yl Oligoglycosides

The alkyl or alkenyl oligoglycosides representing also preferred emulsifiers may be derived from aldoses or ketoses containing 5 or 6 carbon atoms, preferably glucose. Accordingly, the preferred alkyl and/or alkenyl oligoglycosides are alkyl or alkenyl oligoglucosides. These materials are also known generically as "alkyl polyglycosides" (APG). The alk(en)yl oligoglycosides according to the invention correspond to formula (I):

$$R^1O[G]_p \quad (I)$$

wherein $R^1$ is an alkyl or alkenyl radical having from 6 to 22 carbon atoms, G is a sugar unit having 5 or 6 carbon atoms and p is a number from 1 to 10. The index p in general formula (I) indicates the degree of oligomerisation (DP degree), i.e. the distribution of mono- and oligoglycosides, and is a number of 1 to 10. Whereas p in a given compound must always be an integer and, above all, may assume a value of 1 to 6, the value p for a certain alkyl oligoglycoside is an analytically determined calculated quantity which is mostly a broken number. Alk(en)yl oligoglycosides having an average degree of oligomerisation p of 1.1 to 3.0 are preferably used. Alk(en)yl oligoglycosides having a degree of oligomerisation below 1.7 and, more particularly, between 1.2 and 1.4 are preferred from the applicational point of view. The alkyl or alkenyl radical $R^5$ may be derived from primary alcohols containing 4 to 22 and preferably 8 to 16 carbon atoms. Typical examples are butanol, caproic alcohol, caprylic alcohol, capric alcohol, undecyl alcohol, lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol and technical mixtures thereof such as are formed, for example, in the hydrogenation of technical fatty acid methyl esters or in the hydrogenation of aldehydes from Roelen's oxo synthesis. Alkyl oligoglucosides based on hydrogenated $C_8$-$C_{16}$ coconut oil alcohol having a DP of 1 to 3 are preferred. Also suitable are alkoxylation products of alkyl oligoglucosides, for example adducts of 1 to 10 moles ethylene oxide and/or 1 to 5 moles propylene oxide to $C_8$-$C_{10}$ or $C_{12}$-$C_{18}$ alkyl oligoglucoside having a DP between 1.2 and 1.4.

Miscellaneous Emulsifiers

Typical anionic emulsifiers are aliphatic $C_{12-22}$ fatty acids such as palmitic acid, stearic acid or behenic acid, for example, and $C_{12-22}$ dicarboxylic acids such as azelaic acid or sebacic acid, for example. Other suitable emulsifiers are zwitterionic surfactants. Zwitterionic surfactants are surface-active compounds which contain at least one quaternary ammonium group and at least one carboxylate and one sulfonate group in the molecule. Particularly suitable zwitterionic surfactants are the so-called betaines such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocamidopropyl Bewine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH— or —SO$_3$H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine.

Oil Components

In a number of cases it may be also advantageous to add oil components (optional component c2) to the biocide compositions in order to support the emulsification power of the products. Suitable products comprise Guerbet alcohols based on fatty alcohols having 6 to 18, preferably 8 to 10, carbon atoms, esters of linear $C_6$-$C_{22}$-fatty acids with linear or branched $C_6$-$C_{22}$-fatty alcohols or esters of branched $C_6$-$C_{13}$-carboxylic acids with linear or branched $C_6$-$C_{22}$-fatty alcohols, such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$-$C_{22}$-fatty acids with branched alcohols, in particular 2-ethylhexanol, esters of $C_{18}$-$C_{38}$-alkylhydroxy carboxylic acids with linear or branched $C_6$-$C_{22}$-fatty alcohols, in particular Dioctyl Malate, esters of linear and/or branched fatty acids with polyhydric alcohols (such as, for example, propylene glycol, dimerdiol or trimertriol) and/or Guerbet alcohols, triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acids with linear or branched alcohols having 1 to 22 carbon atoms (Cetiol® B) or polyols having 2 to 10 carbon atoms and 2 to 6 hydroxyl groups, vegetable oils, branched primary alcohols, substituted cyclohexanes, linear and branched $C_6$-$C_{22}$-fatty alcohol carbonates, such as, for example, Dicaprylyl Carbonate (Cetiol® CC), Guerbet carbonates, based on fatty alcohols having 6 to 18, preferably 8 to 10, carbon atoms, esters of benzoic acid with linear and/or branched $C_6$-$C_{22}$-alcohols (e.g. Cetiol® AB), linear or branched, symmetrical or asymmetrical dialkyl ethers having 6 to 22 carbon atoms per alkyl group, such as, for example, dicaprylyl ether (Cetiol® OE), ring-opening products of epoxidized fatty acid esters with polyols, silicone oils (cyclomethicones, silicone methicone grades, etc.), aliphatic or naphthenic hydrocarbons, such as, for example, squalane, squalene or dialkylcyclohexanes, and/or mineral oils. The preferred oil components/cosolvents show an ester structure preferably adipates (Cetiol® B, Agnique DiME 6), methyl esters of vegetable oils (Agnique® ME 18RD-F, Agnique® ME 12C-F), alkyl esters (Agnique® Ae 3-2EH), all products available in the market from Cognis GmbH.

INDUSTRIAL APPLICATION

In a final embodiment the present invention refers to a method for controlling undesirable vegetation, comprising applying to the undesirable vegetation a composition comprising
(a) surfactants obtained by reaction of sulphamic acid with at least one of the various alcohol components cited above,
(b) biologically-active ingredients, and optionally
(c) auxiliary agents.

In the following the invention is illustrated in more detail by working examples. Unless otherwise defined, all technical and scientific terms used herein have the same meaning commonly understood by one of ordinary skill in the art to which the invention belongs. Although methods and materials similar or equivalent to those described herein can be used in the practice or testing of the invention, suitable methods and materials are described below. The materials, methods and examples are illustrative only, and are not intended to be limiting.

EXAMPLES

Example 1

One molar equivalent of glycerol was reacted with 2.7 molar equivalents of sulphamic acid (CAS 5329-14-6). The reaction was carried out at atmospheric pressure, at a temperature of 140° C. to 160° C. The reaction was initiated at about 110° C. The resulting sulphate was then neutralized with NH$_4$OH to a pH of 5.5-6.0. The glycerol used was U.S.P. glycerol, and also technical grade (90%) glycerol.

Example 2

One molar equivalent of glycerol was reacted with 3.0 molar equivalents of sulphamic acid (CAS 5329-14-6). The reaction was carried out at atmospheric pressure, at a temperature of 140° C. to 160° C. The reaction was initiated at about 110° C. The resulting sulphate was then neutralized with NH$_4$OH to a pH of 5.5-6.0. The glycerol used was U.S.P. glycerol.

Example 3

One molar equivalent of glycerol was reacted with 3.75 molar equivalents of sulphamic acid (CAS 5329-14-6). The reactions were carried out at atmospheric pressure, at a temperature of 140° C. to 160° C. The reaction was initiated at about 110° C. The resulting sulphate was then neutralized with NH$_4$OH to a pH of 5.5-6.0. The glycerol used was U.S.P. glycerol, and also technical grade (90%) glycerol.

Example 4

One molar equivalent of glycerol was reacted with 4 molar equivalents of sulphamic acid (CAS 5329-14-6). The reactions were carried out at atmospheric pressure, at a temperature of 140° C. to 160° C. The reaction was initiated at about 110° C. The resulting sulphate was then neutralized with NH$_4$OH to a pH of 5.5-6.0. The glycerol used was U.S.P. glycerol.

The invention has been described with reference to specific embodiments. One of ordinary skill in the art, however, appreciates that various modifications and changes can be made without departing from the scope of the invention as set forth in the claims. For example, although herbicides are described herein, the invention may be used as a fungicide, insecticide, miticide, acaricide, and nematocide. Accordingly, the specification is to be regarded in an illustrative manner, rather than with a restrictive view, and all such modifications are intended to be included within the scope of the invention. The benefits, advantages, and solutions to problems have been described above with regard to specific embodiments. The benefits, advantages, and solutions to problems and any element(s) that may cause any benefit, advantage, or solution to occur or become more pronounced are not to be construed as a critical, required, or essential feature or element of any or all of the claims.

What is claimed is:

1. A biologically-active composition comprising: (a) one or more surfactants obtained by reacting a compound with two or more hydroxyl groups selected from the group consisting of polyhydric alcohols, polyols, saccharides, polysaccharides and mixtures thereof, with a sulphating agent, (b) one or more biologically-active ingredients comprising one or more herbicides, and (c) optionally, one or more auxiliary agents.

2. The composition of claim 1, wherein said surfactants (component a) are selected from the group consisting of sulphated polyhydric alcohols, sulphated polyols, sulphated saccharides, sulphated polysaccharides and mixtures thereof.

3. The composition of claim 1, wherein said surfactant (component a) comprises glycerol sulphate.

4. The composition of claim 1, wherein said herbicide comprises glyphosate acid or glufosinate, or a salt or derivative thereof.

5. The composition of claim 1, wherein said auxiliary agent (component c) is present, and is selected from the group consisting of co-surfactants, emulsifiers, oil components, and mixtures thereof.

6. A method for controlling undesirable vegetation, comprising applying to the undesirable vegetation a composition of claim 1.

7. The composition of claim 1, wherein the surfactant comprises a disulphate or a trisulphate or a mixture of monosulphates, disulphates and trisulphates.

8. The composition of claim 3, wherein the sulphating agent comprises sulphamic acid.

9. The composition of claim 3, wherein the composition comprises an auxiliary agent comprising one or more surfactants selected from alkylphenol ethoxylates, alkyl polyglycosides, tallow amine ethoxylates, sorbitan esters, fatty acid esters of glycerol, PEG esters of fatty acids, phosphate esters of alcohols and ethoxylates thereof, amine oxides, alkyl ether sulphates and alcohol ethoxylates.

10. A process for preparing the biologically-active composition of claim 1, the process comprising adding the one or more surfactants (component a) to a composition comprising the one or more herbicides (component b), wherein the surfactants (component a) are added in an amount effective to enhance the activity of the herbicides (component b).

11. The process of claim 10, wherein said compound with two or more hydroxyl groups comprises a polyhydric alcohol containing 2 to 10 carbon atoms.

12. The process of claim 11, wherein said polyhydric alcohol is selected from the group consisting of ethylene glycol, propylene glycol, diethylene glycol, hexylene glycol, decalene glycol, glycerol, polyglycerol and mixtures thereof.

13. The process of claim 10, wherein said compound with two or more hydroxyl groups comprises a polyol containing 2 to 30 carbon atoms.

14. The process of claim 13, wherein said compound with two or more hydroxyl groups is selected from the group consisting of polyethylene glycol, polypropylene glycol and mixtures thereof.

15. The process of claim 10, wherein said compound with two or more hydroxyl groups comprises a saccharide.

16. The process of claim 15, wherein said saccharide is selected from the group consisting of monosaccharides, disaccharides, polysaccharides and mixtures thereof.

17. The process of claim 10, wherein said sulphating agent is selected from the group consisting of sulphuric acid, oleum, chlorosulphonic acid, $SO_3$ gas and sulphamic acid.

18. The process of claim 17, wherein said sulphating agent comprises sulphamic acid.

19. The process of claim 10, wherein said biologically-active ingredient comprises glyphosate acid or glufosinate, or a derivative or salt thereof.

20. The process of claim 10, wherein the surfactant comprises a disulphate or a trisulphate or a mixture of monosulphates, disulphates and trisulphates.

* * * * *